US009085006B2

(12) United States Patent
Wu et al.

(10) Patent No.: US 9,085,006 B2
(45) Date of Patent: Jul. 21, 2015

(54) FRAGRANCE SHOWER

(71) Applicants: XIAMEN SOLEX HIGH-TECH INDUSTRIES CO., LTD., Xiamen, Fujian (CN); Huasong Zhou, Xiamen, Fujian (CN)

(72) Inventors: Yulin Wu, Xiamen (CN); Jianmin Chen, Xiamen (CN); Honghuang Xiong, Xiamen (CN); Huasong Zhou, Xiamen (CN)

(73) Assignees: XIAMEN SOLEX HIGH-TECH INDUSTRIES CO., LTD., Xiamen (CN); Huasong Zhou, Xiamen (CN)

( * ) Notice: Subject to any disclaimer, the term of this patent is extended or adjusted under 35 U.S.C. 154(b) by 97 days.

(21) Appl. No.: 14/056,245

(22) Filed: Oct. 17, 2013

(65) Prior Publication Data

US 2014/0131482 A1     May 15, 2014

(30) Foreign Application Priority Data

Nov. 15, 2012 (CN) .......................... 2012 1 0466969

(51) Int. Cl.
| | |
|---|---|
| *B05B 1/18* | (2006.01) |
| *B05B 3/04* | (2006.01) |
| *B05B 7/24* | (2006.01) |
| *A61L 9/12* | (2006.01) |
| *A61L 9/14* | (2006.01) |

(52) U.S. Cl.
CPC . *B05B 7/24* (2013.01); *A61L 9/122* (2013.01); *A61L 9/145* (2013.01); *B05B 1/18* (2013.01); *B05B 3/04* (2013.01); *A61L 2209/134* (2013.01)

(58) Field of Classification Search
CPC .............. B05B 1/18; B05B 3/04; B05B 7/24; A61L 9/122; E03C 2201/40; Y10S 4/903
See application file for complete search history.

(56) References Cited

U.S. PATENT DOCUMENTS

| | | | | |
|---|---|---|---|---|
| 3,018,969 | A * | 1/1962 | Gentry ........................ | 239/312 |
| 5,957,387 | A * | 9/1999 | Porta et al. .................. | 239/312 |
| 6,006,374 | A * | 12/1999 | Winnett et al. .............. | 4/525 |
| 6,557,782 | B1 * | 5/2003 | Urra ............................ | 239/315 |
| 7,093,775 | B1 * | 8/2006 | Bingham .................... | 239/302 |
| 2006/0039835 | A1 * | 2/2006 | Nottingham et al. ......... | 422/124 |
| 2012/0091231 | A1 * | 4/2012 | Ajagbe ........................ | 239/418 |

FOREIGN PATENT DOCUMENTS

CN     201728163 U     2/2011

* cited by examiner

*Primary Examiner* — Darren W Gorman
(74) *Attorney, Agent, or Firm* — Rabin & Berdo, P.C.

(57) ABSTRACT

A fragrance shower has a shower unit having a body and an outlet cover. The outlet cover covers the body to form a waterway, further includes a fragrance unit connected to the shower unit. The fragrance unit includes an impeller, an accommodating room, a perfume pouch, a fan and a cover. The impeller is disposed inside the shower unit in rotating way and is coupled to the waterway. Water flows through the waterway to rotate the impeller. The cover is disposed with air holes and covers the accommodating room. The perfume pouch and the fan are placed inside the accommodating room, the rotating shaft of the fan is connected to the shaft of the impeller in a driving way, the impeller rotates to drive the fan to rotate. The fan rotates to blow the fragrance of the perfume pouch out.

10 Claims, 8 Drawing Sheets

FRAGRANCE SHOWER

FIELD OF THE INVENTION

The present invention relates to a fragrance shower.

BACKGROUND OF THE INVENTION

In modern society, shower is not just a means to wash dirt off, but an important matters of leisure life and healthy preserving. So that shower head is not just a simple outlet function. A shower is provided in the Chinese patent data with publishing number 200920216685.8 in Feb. 2, 2011. the shower comprising a handle outer, the handle outer is disposed with a perfume box inside. When in use, water flows from one end of the handle outer into the inside, then flows through the perfume box, finally flows out of the other end of the handle outer, so that the water has fragrance of the perfume box.

However, as the perfume box is directly soaked in the water flowing, water continues to flush the perfume box, in one hand, it is a waste of the perfume, shortening the service life of the perfume box; in the other hand, fragrance is adsorped by the water, the perfume is not well sent forth to the air, making it with failure fragrance effect.

SUMMARY OF THE INVENTION

The present invention is provided with a fragrance shower with long service life and well fragrance effect, it overcomes the disadvantages of the existing technology.

The technical proposal of the present invention to solve the technical problems is as below:

A fragrance shower, comprising a shower unit, the shower unit comprising a body and an outlet cover, the outlet cover covers the body to form a waterway, wherein:

further comprising a fragrance unit connected to the shower unit, the fragrance unit comprising an impeller, an accommodating room, a perfume pouch, a fan and a cover, the impeller is disposed inside the shower unit in rotating way and coupled to the waterway, water flows through the waterway to impact the impeller to rotate; the cover is disposed with air holes, the cover covers the accommodating room, the perfume pouch and the fan are placed inside the accommodating room, the rotating shaft of the fan is connected to the shaft of the impeller in driving way, the impeller rotates to drive the fan to rotate, the fan rotates to blow the fragrance of the perfume pouch out.

In another preferred embodiment, the central of the outlet cover is disposed with a recess, the accommodating room is held inside the recess.

In another preferred embodiment, the external end of the shaft of the impeller is disposed with a clutch, the external end of the rotating shaft of the fan is disposed with an apposition clutch, the clutch is connected to the apposition clutch.

In another preferred embodiment, the clutch is two pins disposed in the end of the shaft of the impeller, the apposition clutch is two apposition pins disposed in the end of the rotating shaft of the fan, the two pins and two apposition pins are inserted to each other, the ends of the two pins and two apposition pins are smoothed.

In another preferred embodiment, the accommodating room is disposed with several through holes, the blades of the fan are near to the cover, the shower unit further comprising an inclining body, which is placed inside the body, water flows through the inclining body to impact the impeller to drive the impeller to rotate.

In another preferred embodiment, the fragrance unit further comprising a storage room and a lid, the perfume pouch is put inside the storage room and is covered by the lid, the storage room is disposed with several volatilization windows, the fragrance unit further comprising a rotating part to optionally open or close the volatilization windows, the rotating part is disposed with window blades corresponding to the volatilization window, the rotating part is disposed with a handle, the handle is extended out of the cover.

In another preferred embodiment, the perfume pouch is an oil clot to adsorp perfume, the accommodating room is disposed with a feeding hole corresponding to the oil clot.

In another preferred embodiment, the outlet cover is disposed with upper magnet, the accommodating room is disposed with lower magnet, the upper magnet is attracted the lower magnet. In another preferred embodiment, the outlet cover is disposed with elastic hooks, the accommodating room is disposed with lock grooves, the elastic hooks are respectively locked to the lock grooves.

In another preferred embodiment, the outlet cover is disposed with overhead hooks, the accommodating room is disposed with protruding ribs, the overhead hooks are respectively locked to the protruding ribs.

Compared to the existing technology, the technical proposal of the present invention has advantages as below:

1. water flows through the waterway to impact the impeller to drive the impeller to rotate, the cover is disposed with air holes, the rotating shaft of the fan is connected to the shaft of the impeller, and the impeller rotates to drive the fan to rotate, the fan rotates to blow the fragrance of the perfume pouch out. In one hand, the perfume pouch is off the water, the volatilization speeds up until the fan rotates, otherwise it would not lose its work, so that it has advantages of material saving and long service life. In the other hand, the perfume is blown out but not dissolved in the water, making the shower room full with fragrance, the present invention has well fragrance effect.

2. the central of the outlet cover is disposed with a recess, the accommodating room is placed inside the recess, so that the fragrance unit is directly faced to the bather, it has well fragrance effect and high maternal usage rate.

3. the clutch is connected to the apposition clutch, so that the shaft of the impeller rotates synchronously with the rotating shaft of the fan.

4. the two pins and two apposition pins are inserted to each other, the structure is simple. The ends of the pins and the apposition pins are smoothed, so that it is convenient to insert in any intersection angle, that is to say, when the fragrance unit is put into the recess of the shower unit, the intersection is implemented.

5. the blades of the fan are near to the cover, so that the air flowing is blown to the face of the bather, a fragrance breeze is stroking the face.

6. the rotating part is optionally to open or close the volatilization window, the volatilization window is closed when not in use, preventing volatilization of the perfume. The rotating part is disposed with a handle, the handle is extended out of the cover, so that it is convenient to operate the rotating part.

7. the perfume pouch is an oil clot to adsorp perfume, the accommodating room is disposed with a feeding hole corresponding to the oil clot, so that it is convenient to feed perfume to the oil clot.

8. the outlet cover is disposed with upper magnet, the accommodating room is disposed with lower magnet, the upper magnet attracts the lower magnet, so that the fragrance unit is detached from the shower unit conveniently.

BRIEF DESCRIPTION OF THE DRAWINGS

The present invention will be further described with the drawings and the embodiments.

DETAILED DESCRIPTION OF THE EMBODIMENTS

Figure 1:
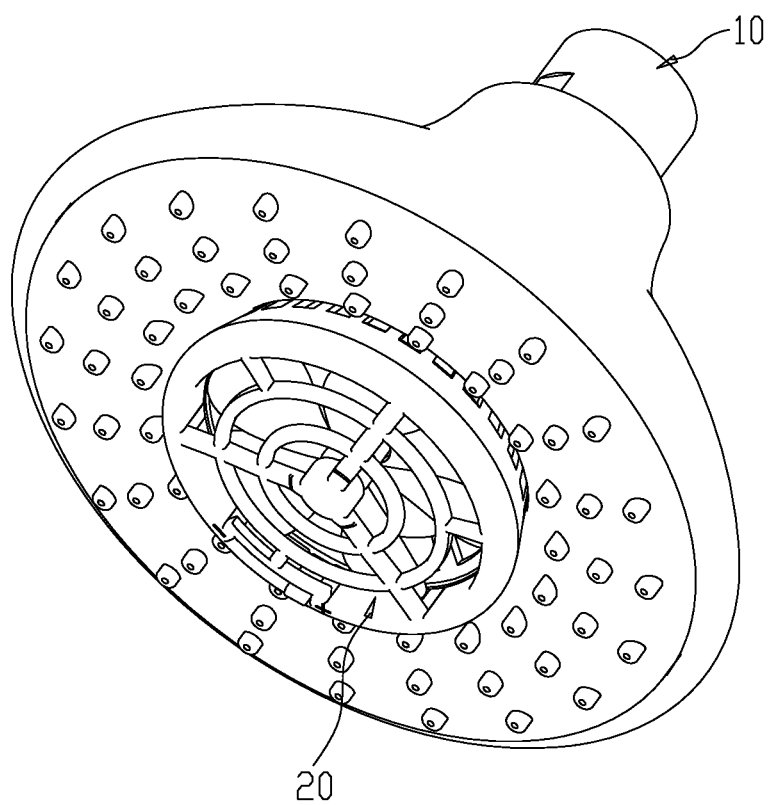
FIG. 1 illustrates the structure of a fragrance shower of the first embodiment of the present invention.
Figure 2:
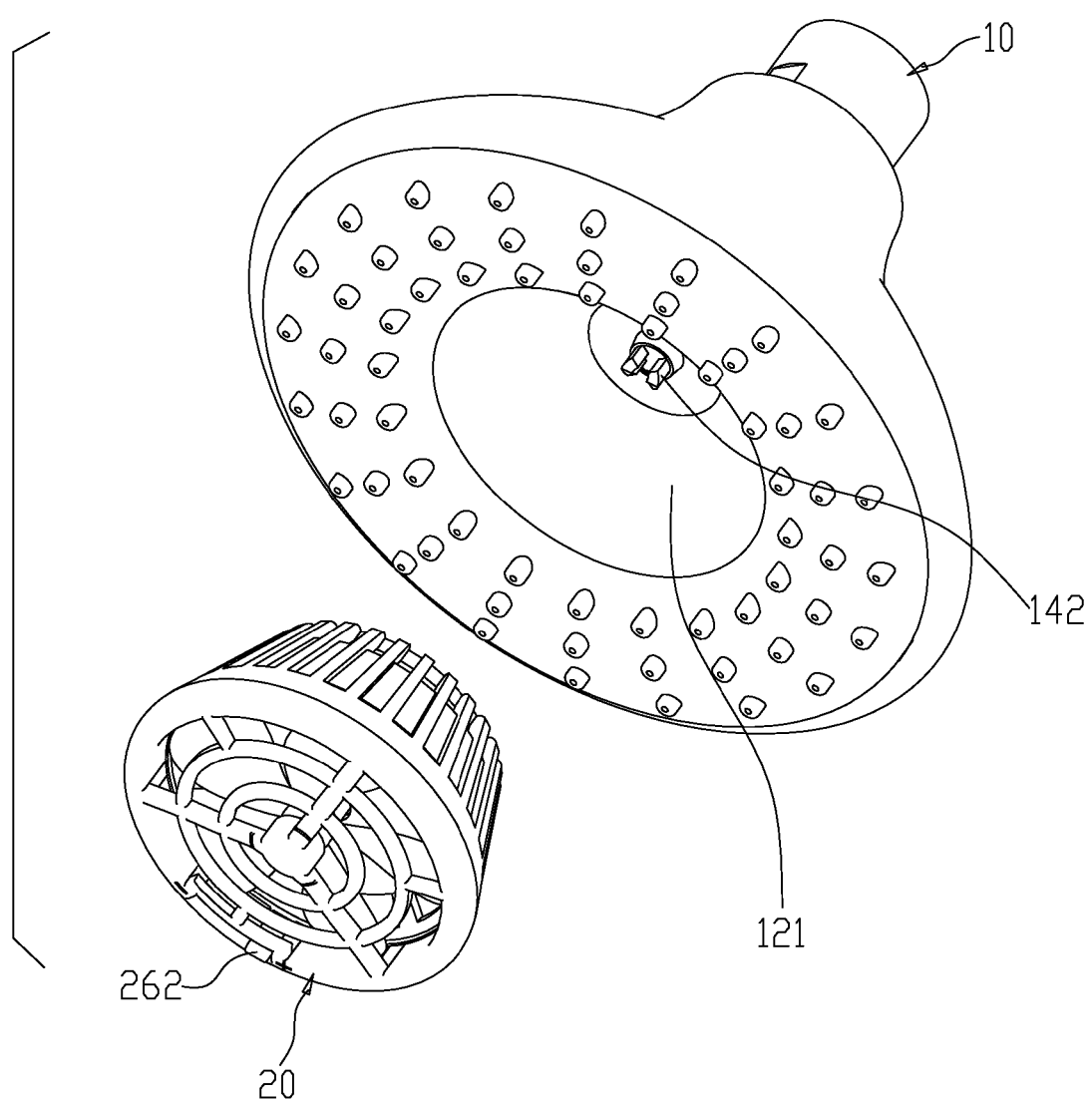
FIG. 2 illustrates the breakdown structure of the fragrance shower of FIG. 1.

Refer to FIG. 1 and FIG. 2, a fragrance shower of the present invention comprising a shower unit 10 and a fragrance unit 20. the fragrance unit 20 is disposed outside the shower unit 10. The shower unit 10 is used to spray water for shower. The fragrance unit 20 is used to send forth fragrance to make the shower room scented with fragrance.

Figure 3:
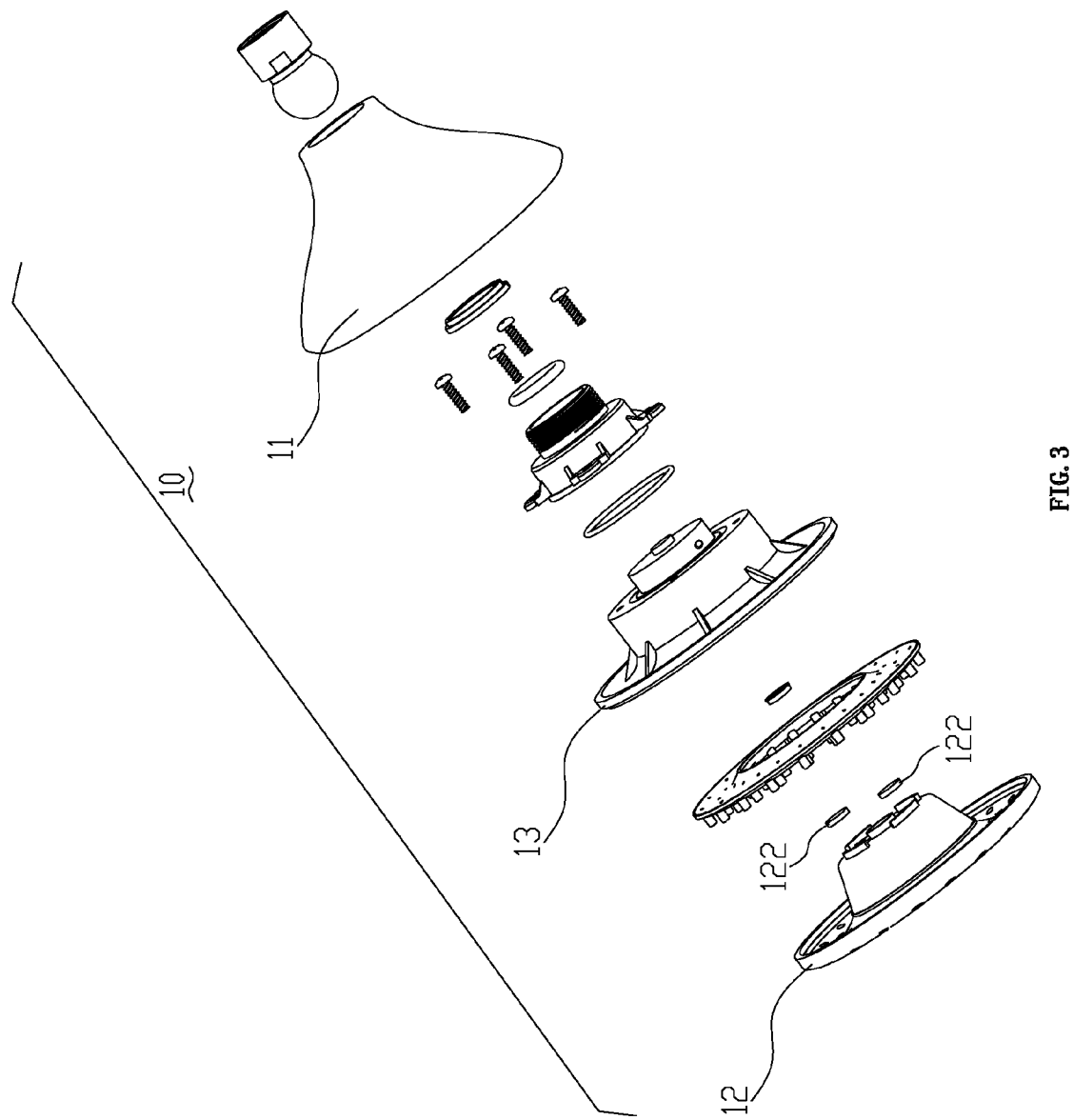
FIG. 3 illustrates the breakdown structure of the shower unit of the fragrance shower of FIG. 1.

Refer to FIG. 2 and FIG. 3, the shower unit 10 comprising a body 11, an outlet cover 12 and an inclining body 13. The central of the outlet cover 12 is concaved with a recess 121. the outlet cover 12 is disposed with two upper magnets 122 at the bottom surface of the recess 121. please refer to FIG. 6, the outlet cover 12 covers the body 11 to form a waterway 15. the inclining body 13 is received inside the body 11.

Figure 4:
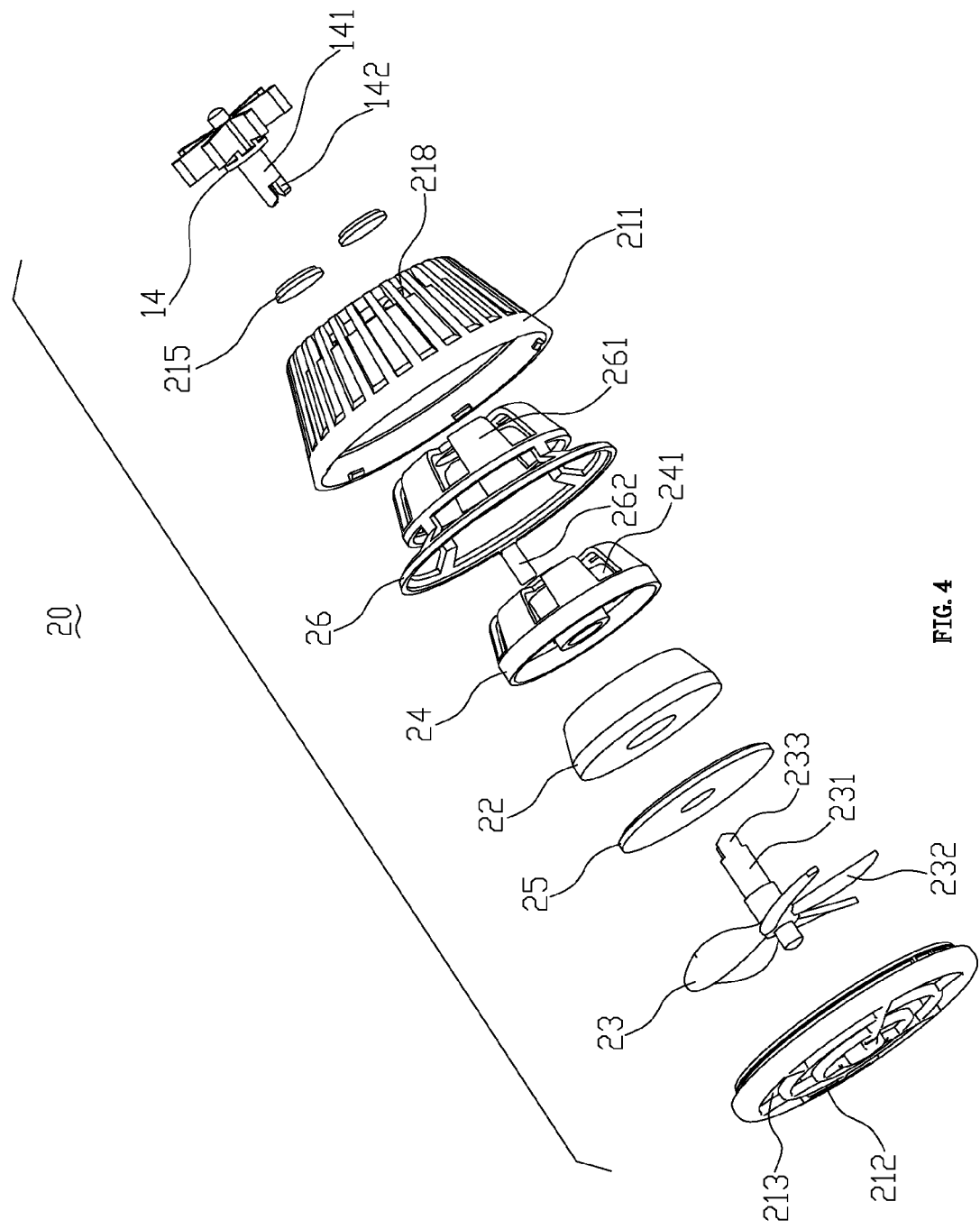
FIG. 4 illustrates the breakdown structure of the fragrance unit of the fragrance shower of FIG. 1.
Figure 5:
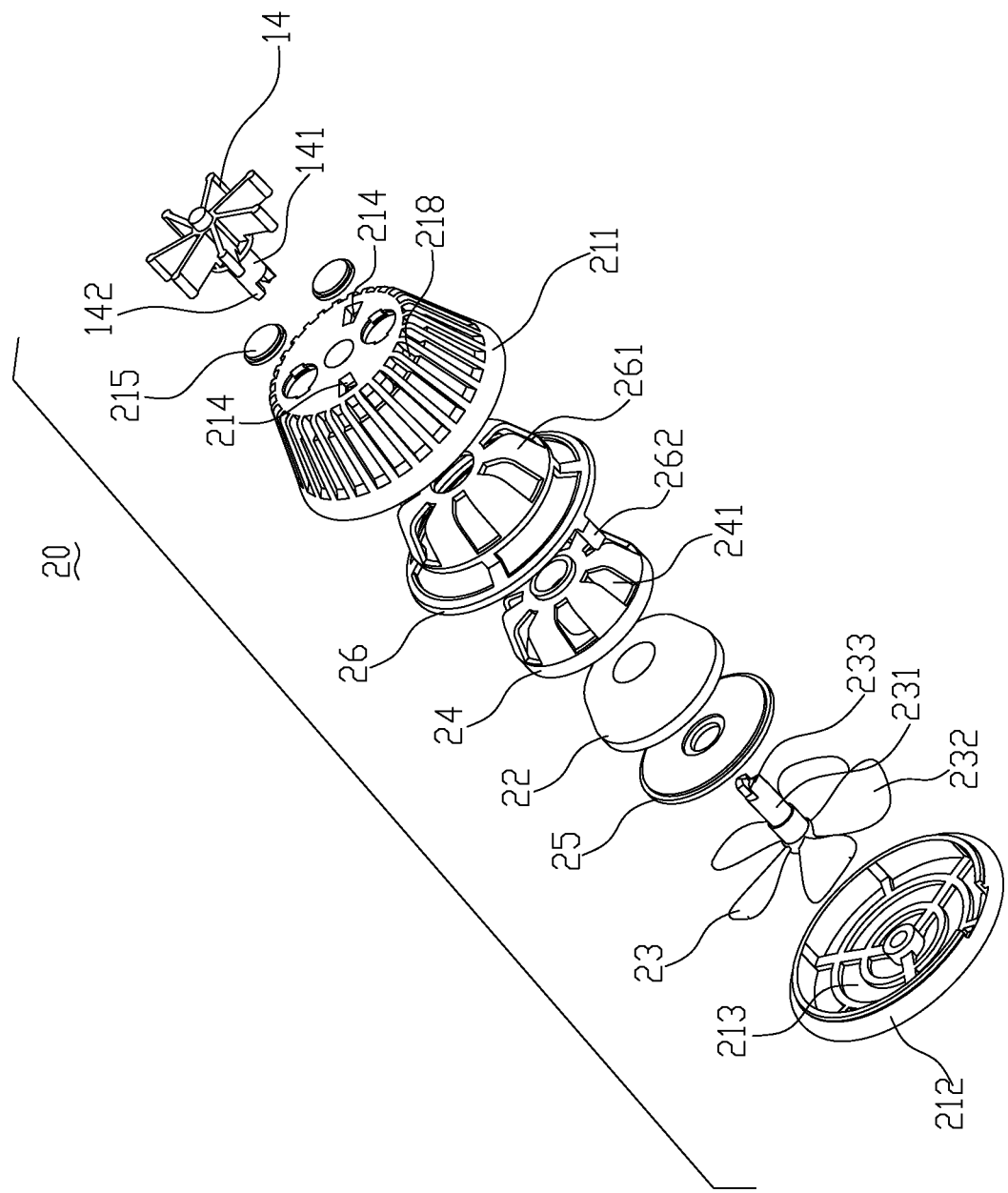
FIG. 5 illustrates the breakdown structure of the fragrance unit of the fragrance shower of FIG. 1 in another view angle.

Refer to FIG. 4 and FIG. 5, the fragrance unit 20 comprising an impeller 14, an accommodating room 211, a cover 212, a perfume pouch 22, a fan 23, a storage room 24, a lid 25 and a rotating part 26.

The external end of the shaft 141 of the impeller 14 is disposed with a clutch 142, the clutch 142 is two pins disposed in the end of the shaft 141 of the impeller 14, and the ends of the pins are smoothed.

The accommodating room 211 is disposed with several through holes 218 and the cover 212 are disposed with several air holes 213. the top of the accommodating room 211 corresponding to the perfume pouch 22 is disposed with two feeding holes 214. the top of the accommodating room 211 corresponding to the upper magnets is disposed with two lower magnets 215.

Preferred, the perfume pouch 22 is an oil clot to absorp perfume.

The fan 23 comprising a rotating shaft 231 and several blades 232. the external end of the rotating shaft 231 is disposed with an apposition clutch 233 corresponding to the clutch 142, the apposition clutch 233 is two apposition pins disposed in the end of the rotating shaft 231, the ends of the apposition pins are smoothed.

The storage room 24 is disposed with several volatilization windows 241.

The rotating part 26 is optional to open or close the volatilization windows. The rotating part 26 is disposed with several window blades 261 and a handle 262. the window blades 261 are corresponding to the volatilization windows 241.

Figure 6:
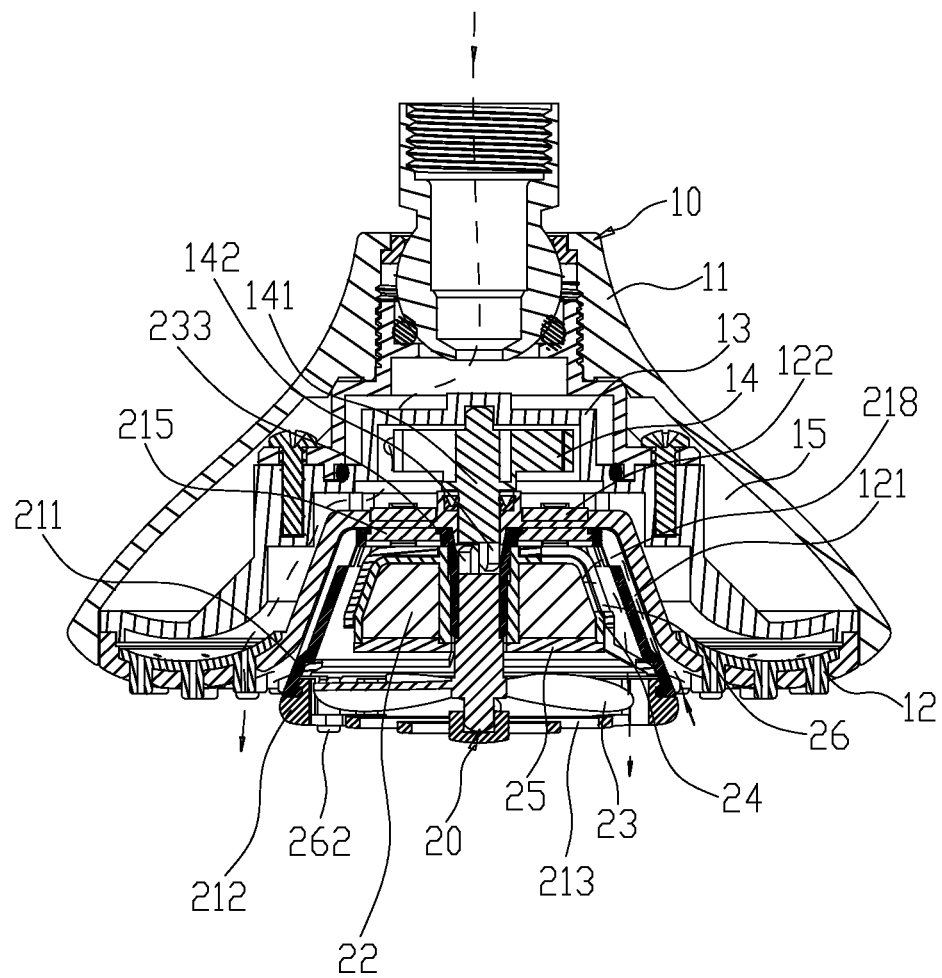
FIG. 6 illustrates the sectional view of the fragrance shower of FIG. 1.

As figured in FIG. 4 to FIG. 6, the impeller 14 is disposed inside the body 11, and the blades of the impeller 14 is disposed inside the inclining body 13, the shaft 141 of the impeller 14 is extended out of the outlet cover 12.

The perfume pouch 22 is put inside the storage room 24 and is covered by the lid 25; the rotating part 26 covers the storage room 24; the rotating part 26 and the fan 23 are received inside the accommodating room 211; the perfume pouch 22, the fan 23, the storage room 24, the lid 25 and the rotating part 26 are covered inside the accommodating room 211 by the cover 212, the blades 232 of the fan 23 is near to the cover 212; the handle 262 is extended out of the cover 212.

Please refer to FIG. 6, the accommodating room 211 is disposed inside the recess 121; the clutch 142 is connected to the apposition clutch 233, that is to say, two pins and two apposition pins are inserted to each other, so that the rotating shaft 231 of the fan 23 is connected to the shaft 141 of the impeller 14 in driving way; two upper magnet 122 are contracted the lower magnets 215.

When in use, water flows through the inclining body 13 to impact the impeller 14 to drive the impeller 14 to rotate; the shaft 141 of the impeller 14 drives the rotating shaft 231 of the fan 23 to rotate synchronously, when the fan 23 rotates, the air flows from the clearance of the fragrance unit 20 and the shower unit 10, then flows out from the air holes 213 of the cover 212.

Figure 7:
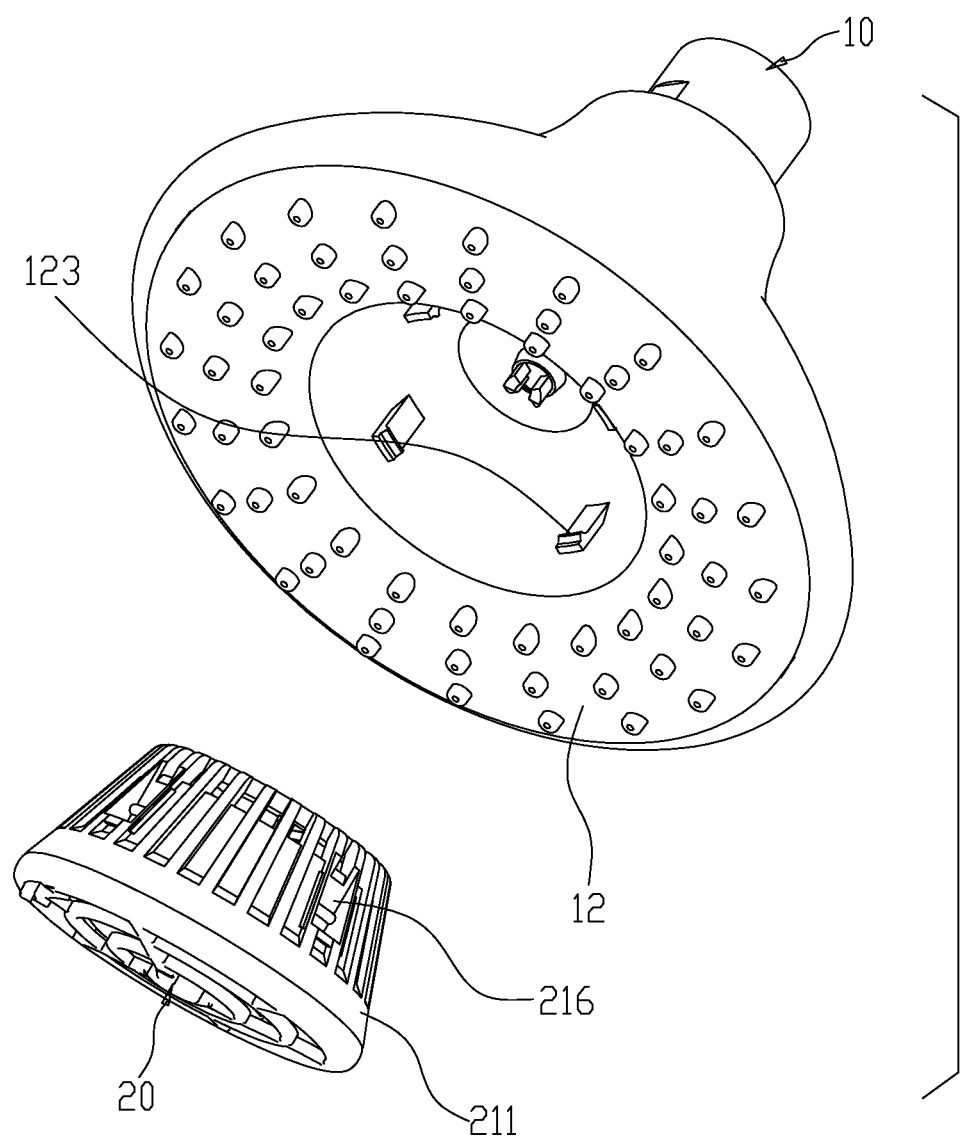
FIG. 7 illustrates the breakdown structure of a fragrance shower of the second embodiment of the present invention.

As figured in FIG. 7 of the breakdown structure of the second embodiment of the present invention, the difference of the fragrance shower from the first embodiment is that the outlet cover 12 is disposed with several elastic hooks 123, the accommodating room 211 is disposed with several lock grooves 216, the elastic hooks 123 are respectively locked to the lock grooves 216, so that the fragrance unit 20 is detachably connected to the shower unit 10.

Figure 8:
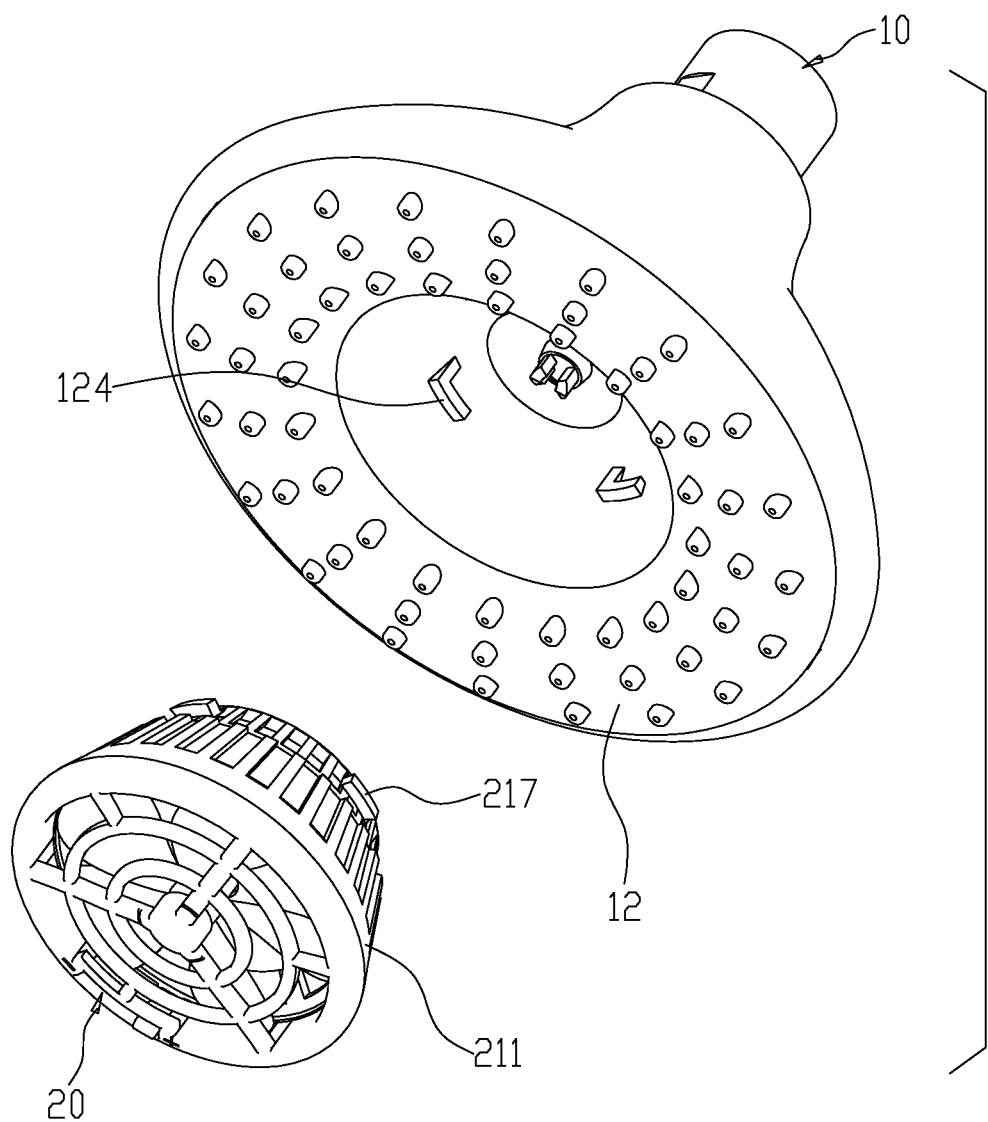
FIG. 8 illustrates the breakdown structure of a fragrance shower of the third embodiment of the present invention.

As figured in FIG. 8 of the breakdown structure of the third embodiment of the present invention, the difference of the fragrance shower from the first embodiment is that the outlet cover 12 is disposed with several overhead hooks 124, the accommodating room 211 is disposed with several protruding ribs 217, the overhead hooks 124 are respectively locked to the protruding ribs 217, so that the fragrance unit 20 is detachably connected to the shower unit 10.

Although the present invention has been described with reference to the preferred embodiments thereof for carrying out the patent for invention, it is apparent to those skilled in the art that a variety of modifications and changes may be made without departing from the scope of the patent for invention which is intended to be defined by the appended claims.

The invention claimed is:

1. A fragrance shower, comprising:
   a shower unit, the shower unit comprising a body and an outlet cover, the outlet cover covering the body to form a waterway; and
   a fragrance unit connected to the shower unit, the fragrance unit comprising an impeller with a shaft, an accommodating room, a perfume pouch, a fan with a rotating shaft, and a cover; wherein the impeller is rotatably disposed inside the shower unit and coupled to the waterway, whereby water flows through the waterway to impact the impeller to rotate; wherein the cover includes air holes, the cover covering the accommodating room; wherein the perfume pouch and the fan are located inside the accommodating room; and wherein the rotating shaft of the fan is drivingly connected to the shaft of the impeller whereby the impeller rotates to drive the fan to rotate, and the fan rotates to blow a fragrance of the perfume pouch out through the air holes of the cover.

2. A fragrance shower according to claim 1, wherein the outlet cover includes a centrally disposed recess, and the accommodating room is held inside the recess.

3. A fragrance shower according to claim 2, wherein an external end of the shaft of the impeller includes a clutch, and an external end of the rotating shaft of the fan includes an apposition clutch, and wherein the clutch is connected to the apposition clutch.

4. A fragrance shower according to claim 3, wherein the clutch includes two pins disposed at the end of the shaft of the impeller, and the apposition clutch includes two apposition pins disposed at the end of the rotating shaft of the fan, and wherein the two pins and the two apposition pins are inserted to each other, and the ends of the two pins and two apposition pins are smoothed.

5. A fragrance shower according to claim 1, wherein the accommodating room defines several through holes, and wherein blades of the fan are located proximate the cover; the shower unit further comprising: an inclining body, which is located inside the body, such that water flows through the inclining body to impact the impeller to drive the impeller to rotate.

6. A fragrance shower according to claim 5, wherein the fragrance unit further comprises a storage room and a lid, and the perfume pouch is located inside the storage room and is covered by the lid, the storage room defining several volatilization windows, and wherein the fragrance unit further comprises a rotating part configured to open and close the volatilization windows, the rotating part defining window blades corresponding to the volatilization windows, and the rotating part including a handle, wherein the handle is extended out of the cover.

7. A fragrance shower according to claim 6, wherein the perfume pouch is an oil clot to adsorp perfume, the accommodating room including a feeding hole corresponding to the oil clot.

8. A fragrance shower according to claim 7, wherein the outlet cover includes an upper magnet, and the accommodating room includes a lower magnet, and wherein the upper magnet is attracted to the lower magnet to connect the fragrance unit to the shower unit.

9. A fragrance shower according to claim 7, wherein the outlet cover includes elastic hooks, and the accommodating room includes lock grooves, and wherein the elastic hooks are respectively locked to the lock grooves to connect the fragrance unit to the shower unit.

10. A fragrance shower according to claim 7, wherein the outlet cover includes overhead hooks, and the accommodating room includes protruding ribs, and wherein the overhead hooks are respectively locked to the protruding ribs to connect the fragrance unit to the shower unit.

\* \* \* \* \*